(12) United States Patent
Figueredo (10) Patent No.: US 10,987,090 B2
(45) Date of Patent: Apr. 27, 2021

(54) METHOD OF OBTAINING BIOLOGICAL MATERIAL VIA BIOLOGICAL SAMPLING DEVICE

(71) Applicant: Ariel Figueredo, North Fort Myers, FL (US)

(72) Inventor: Ariel Figueredo, North Fort Myers, FL (US)

( * ) Notice: Subject to any disclaimer, the term of this patent is extended or adjusted under 35 U.S.C. 154(b) by 643 days.

(21) Appl. No.: 15/659,437

(22) Filed: Jul. 25, 2017

(65) Prior Publication Data
US 2017/0319187 A1   Nov. 9, 2017
US 2020/0170629 A9   Jun. 4, 2020

Related U.S. Application Data

(63) Continuation of application No. 13/945,380, filed on Jul. 18, 2013, now abandoned.

(60) Provisional application No. 61/741,376, filed on Jul. 18, 2012.

(51) Int. Cl.
*A61B 10/02*   (2006.01)

(52) U.S. Cl.
CPC .. *A61B 10/0291* (2013.01); *A61B 2010/0216* (2013.01)

(58) Field of Classification Search
CPC ............ A61B 10/02; A61B 2010/0216; A61B 17/425–435; A61B 10/0291; A61B 2010/0074; A61M 2210/14–1441; C12M 1/30

See application file for complete search history.

(56) References Cited

U.S. PATENT DOCUMENTS

| | | | | |
|---|---|---|---|---|
| 4,586,604 A * | 5/1986 | Alter | ...................... | A61B 10/02 206/209 |
| 5,535,756 A * | 7/1996 | Parasher | ................ | A61B 10/02 600/569 |
| 5,792,074 A * | 8/1998 | Turkel | ................... | A61B 10/02 600/569 |
| 7,144,377 B2 * | 12/2006 | Lu | ...................... | A61B 10/0291 600/572 |
| 2004/0014222 A1 * | 1/2004 | Towne | ................. | C12Q 1/6841 436/17 |
| 2014/0194777 A1 * | 7/2014 | Scampini | ............... | A61B 10/02 600/572 |

* cited by examiner

*Primary Examiner* — Devin B Henson
*Assistant Examiner* — H. Q. Nguyen
(74) *Attorney, Agent, or Firm* — George F. Wallace; Thomas Champagne (57) ABSTRACT

A method of using a biological sampling device to obtain a biological sample. The device comprises a sheath, an applicator, a collector, and a handle. The method includes inserting a first applicator end into an organism with the device being in a pre-sampling configuration; transitioning the device from the pre-sampling configuration to a sampling configuration; with the device in the sampling configuration, via the handle, moving the collector against biological material within the organism to collect the biological material; transitioning the device from the sampling configuration to a post-sampling configuration; and with the device in the post-sampling configuration, withdrawing the device from within the organism.

5 Claims, 7 Drawing Sheets

METHOD OF OBTAINING BIOLOGICAL MATERIAL VIA BIOLOGICAL SAMPLING DEVICE

CROSS REFERENCE TO RELATED DOCUMENTS

This document is related to, claims the priority benefit of, and incorporates by reference in its entirety, co-pending U.S. patent application Ser. No. 13/945,380, entitled "Biological Testing Device and Methods of Using and Testing," and filed on Jul. 18, 2013 by Ariel Figueredo, which is related to, claimed the priority benefit of, and incorporated by reference in its entirety, "U.S. Provisional Patent Application Ser. No. 61/741,376, entitled "Biological Sampling Device and Methods of Using and Testing," and filed on Jul. 18, 2012 by Ariel Figueredo.

INVENTOR

Ariel Figueredo

Field of Invention

Generally, the present invention relates to devices and methods for obtaining biological samples from organisms for medical screening, such as devices and methods for obtaining biological samples from female humans for Papanicolaou Tests.

Background of the Invention

A Papanicolaou Test ("Pap Test") is a gynecological screening test that can be used to detect cancerous processes and other abnormalities in the endocervical canal. Procedurally, this test involves the use of a speculum by a medical professional to create a sufficiently sized opening in the vagina of a patient to provide non-interfering entry and exit access to target areas, such as the outer opening of the cervix and the endocervix. A plastic-fronded broom, or a spatula and brush combination, can then be used to frictionally contact a target area for collection of biological matter for testing.

SUMMARY OF THE INVENTION

It is, therefore, an object of the present invention to provide a biological testing device and related methods of using and testing.

The present invention includes a biological sampling device for collecting biological material from within an organism, and related methods of using such a device, preparing a biological sample from such a device, and testing a biological sample prepared from such a device.

Perceived benefits of the present invention can include any combination of the following: reduced discomfort, improved sampling accuracy, improved sampling speed, improved testing accuracy, and improved sampling and/or testing availability. However, it is expressly set forth that these benefits are not intended as exclusive. Thus, any express, implied, or apparent benefit from the disclosure herein and/or use of the present invention is expressly deemed as applicable to the present invention.

In an exemplary embodiment of the present invention, a biological sampling device for collecting biological material from within an organism can include a sheath, a collector, and a handle.

In an exemplary aspect of the present invention, a sheath can include a first sheath end, a second sheath end, and a sheath cavity that extends between the first and second sheath ends.

In another exemplary aspect of the present invention, a collector can include an abrasive outer surface area, and can be configured to transition between a secured position, in which the collector is positioned within the sheath cavity, and a sampling position, in which said collector is positioned outside of the sheath cavity.

In a further exemplary aspect of the present invention, a handle can include a first handle end and a second handle end, and can extend through the sheath cavity with the first handle end being fixed to the collector and the second handle end extending from the second sheath end.

In yet another exemplary aspect of the present invention, when the first sheath end is inserted into an organism through an orifice of the organism, the handle and the sheath can be configured to transition the collector from the secured position to the sampling position; the handle can be configured to move the collector when in the sampling position, such that the outer surface area collects the biological material by abrasively contacting an internal portion of the organism, and the handle and the sheath can be configured to transition the collector from the sampling position to the secured position.

In another exemplary embodiment of the present invention, a biological sampling device can optionally include an applicator having a first applicator end, a second applicator end, and an applicator cavity that extends between the first and second applicator ends, with the applicator being configured to be disposed within the sheath cavity.

In this embodiment of the present invention, a secured position can include the collector being positioned within at least one of the sheath and applicator cavities, and a sampling position can include the collector being positioned outside of the sheath and applicator cavities.

In an exemplary aspect of this embodiment of the present invention, when at least one of the first sheath end and the first applicator end is inserted into the organism through an orifice of the organism and the collector is in the secured position, at least two of the handle, the sheath, and the applicator can be configured to transition the collector from the secured position to the sampling position, the handle is configured to move the collector when in the sampling position, such that the outer surface area can collect the biological material by abrasively contacting an internal portion of the organism, and a plurality of the handle, the sheath, and the applicator can be configured to transition the collector from the sampling position to the secured position.

In a further exemplary embodiment of the present invention, a method of using any biological sampling device enabled herein can include inserting the first applicator end into an organism via an orifice of the organism, with the device being in a pre-sampling configuration such that the first applicator end extends beyond the first sheath end and the collector being disposed within the applicator cavity; with the device disposed within the organism, transitioning the device from the pre-sampling configuration to a sampling configuration by moving the applicator towards the second handle end with the collector being in a static position such that the collector extends through and beyond the first applicator end and is positioned outside of the applicator and sheath cavities; with the device in the sampling configuration, via the handle, moving the collector against an internal portion of the organism to collect biological material within the organism; with the device within the organism, transitioning the device from the sampling configuration to a post-sampling configuration by moving the collector and the first applicator end through the first sheath end and into the sheath cavity with the sheath being in a static position; and with the device in the post-sampling configuration, withdrawing the device from within the organism.

In another exemplary embodiment of the present invention, a method of preparing a biological sample from biological material collected by any biological sampling device enabled herein can include moving a transfer material against a collector to transfer at least a portion of the collected biological material to the transfer material; and after the step of moving, providing the transfer material and the at least a portion of the collected biological matter as the biological sample.

In still another exemplary embodiment of the present invention, a method of testing a biological sample obtained from any biological sampling device enabled herein can include applying at least one testing protocol to the biological sample; and deriving a testing result from the at least one protocol.

The following non-exhaustive list of optional exemplary aspects of the present invention can be applied to any embodiment enabled herein: a sheath can have a continuous exterior sheath surface; a sheath and/or an applicator can be cylindrically shaped; a sheath and/or an applicator can be provided as a combination of multiple shapes; a sheath and/or an applicator can be formed, at least in part, from a plastic; a sheath and/or an application can be provided with a smooth exterior portion; a first sheath end and/or a first applicator end can be tapered or rounded; a first sheath end and/or a first applicator end can include one or more petals; at least a portion of a sheath cavity and/or an applicator cavity can be cylindrical; a sheath cavity and/or an applicator cavity can be coaxial with a sheath; the sheath cavity and/or the applicator cavity can have a non-uniform shape; a collector can be symmetric or asymmetric around at least one axis when in a sampling position and/or a secured position; a collector can include one or more bristles; a collector can deform when in the secured position; a collector can increase in size when transitioned from a secured position to a sampling position; a handle can be adapted to disengage from a collector; a second applicator end can extend from a second sheath end; a sheath, an applicator, and/or a handle can include a respective extension at respective second ends thereof; at least one of a sheath extension, an applicator extension, and/or a handle extension can be configured to abut and/or engage with another of a sheath extension, an applicator extension, and a handle extension to limit relative motion thereof in at least one direction; a collector can be positioned inside a sheath and/or an applicator after the sheath and/or applicator is inserted into an orifice of an organism; a collector can be adapted to remain within a sheath and/or an applicator when the collector is withdrawn from an orifice of an organism; a collector can be configured to be withdrawn from an orifice of an organism while a sheath and/or an applicator remains inserted in an orifice of an organism; a biological sampling device can optionally include at least one of a sealing structure and a stopping structure; a sealing structure or a stopping structure can include at least one of a thread, a cap, an annular groove, a collar, a shoulder, a ridge, a gasket, and a protrusion; a thread can be an open thread or a closed thread; a stopping structure can be configured to limit relative motion of at least two of a sheath, an applicator, a handle, and a collector; a transfer material can include a liquid, a solid, or a gas; and a testing protocol can be associated with a Papanicolaou Test.

These and other exemplary aspects of the present invention are described herein.

BRIEF DESCRIPTION OF THE DRAWINGS

The present invention is illustrated by way of example, and not in limitation, in the figures of the accompanying drawings, in which:

FIG. 5d illustrates an exemplary device in a post-use configuration in which collector 120 is in a secured position and optionally sealed via cap 115a.

DETAILED DESCRIPTION

The invention will now be described in more detail by way of example with reference to the embodiments shown in the accompanying figures. It should be kept in mind that the following described embodiments are only presented by way of example and should not be construed as limiting the inventive concept to any particular physical configuration, material, or order.

Further, it is important to note that this disclosure includes a plurality of elements and/or aspects, and such elements and/or aspects need not be interpreted as necessarily being conjunctively required by one or more embodiments of the present invention. Rather, all combinations of the one or more elements and/or aspects are intended to potentially enable a separate embodiment of the present invention, which are free to be claimed with particularity in this or one or more future filed applications. Moreover, any particular materials, structures, and/or sizes disclosed, expressly or implicitly, herein are to be construed strictly as illustrative and enabling. Therefore, it is expressly set forth that such materials, structures, and/or sizes independently or in any combination of one of more thereof, are merely illustratively representative of one or more embodiments and/or aspects of the present invention and are not to be construed as necessary in a strict sense.

Further, to the extent the same element or aspect is defined differently anywhere within this disclosure, the broader definition is to take absolute precedence, with the distinctions encompassed by the narrower definition to be strictly construed as optional.

The present invention can be embodied in a biological sampling device for collecting biological material from within an organism, and related methods of using such a device and of testing of such material collected by such a device.

Further, the present invention can be utilized on any organism having an orifice, and moreover, the present invention can be utilized by any type of human, such as a non-medically trained individual, a medically trained individual, a doctor, a medical specialist, a nurse, a scientist, a technician, a layperson, and/or a person undergoing biological sampling via the present invention.

Notably, the present invention can be provided in different sizes, including overall width, height, length, and/or diameter, which can be based on the particular application of the present invention. Moreover, the present invention can be utilized to sample biological matter through any available orifice of an organism.

Figure 1:
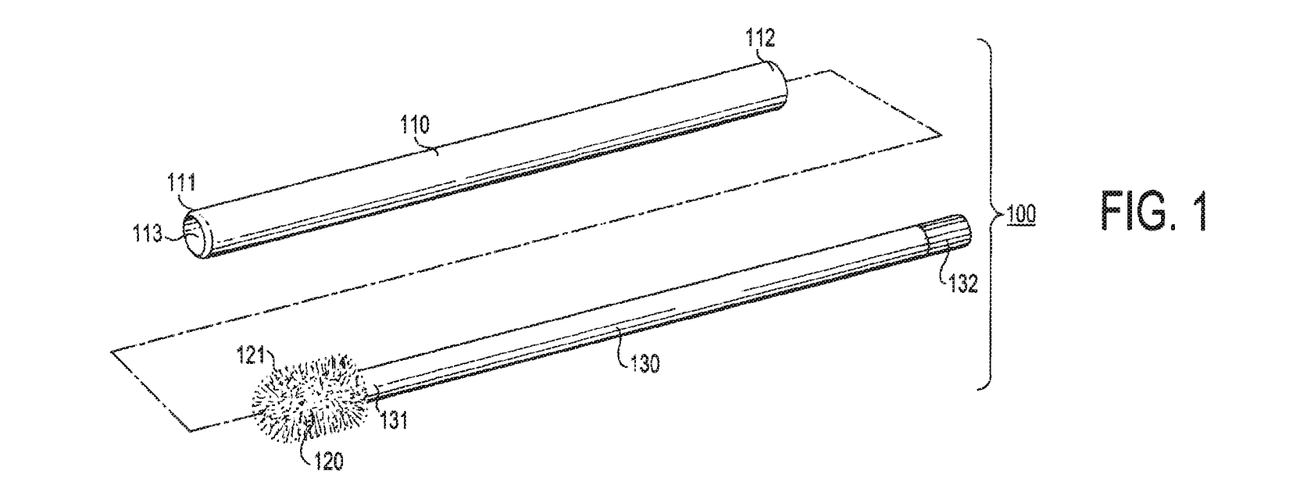
FIG. 1 illustrates an exploded view of an exemplary embodiment of the present invention, in which a biological sampling device 100 can include a sheath 110, a collector 120, and a handle 130.

FIG. 1 illustrates an exploded view of an exemplary embodiment of the present invention, in which a biological sampling device 100 can include a sheath 110, a collector 120, and a handle 130.

In an exemplary aspect of the present invention, sheath 110 can have a first sheath end 111, a second sheath end 112, and a sheath cavity 113 that can extend between the first and second sheath ends. In another exemplary aspect of the present invention, collector 120 can have an abrasive outer surface area 121 that can contact and collect biological material from an internal portion of an organism. In a further exemplary aspect of the present invention, handle 130, can be configured to extend through sheath cavity 113, and can have a first handle end 131 fixed to collector 120 and a second handle end 132 that can extend from second sheath end 112 when the handle is so disposed within the sheath cavity.

Figures 2A, 2B:
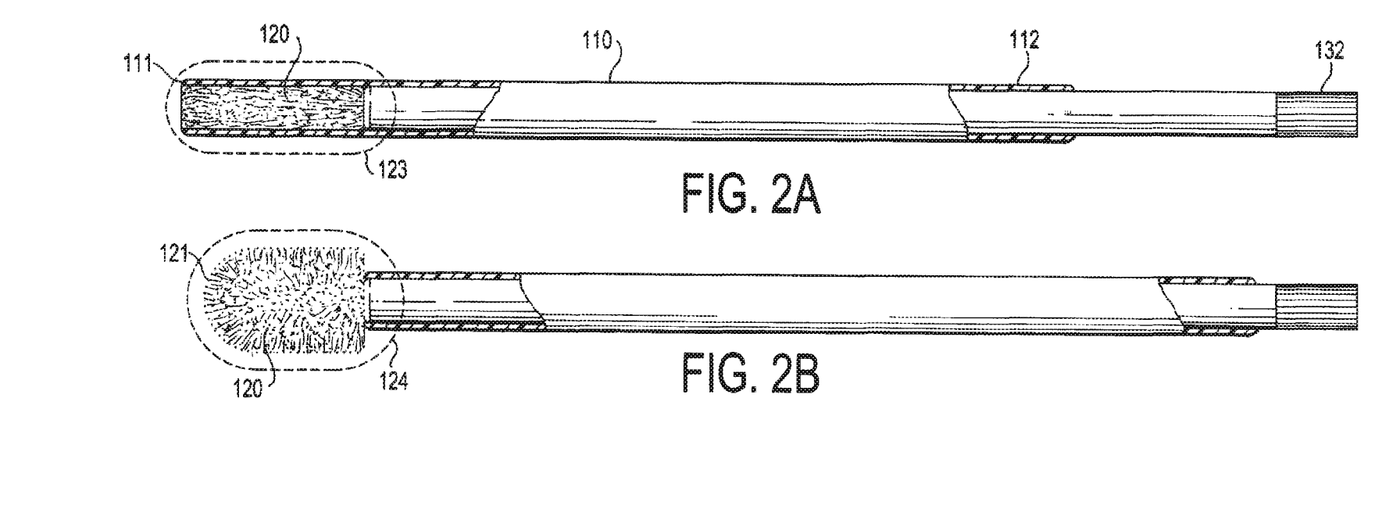
FIG. 2a illustrates an assembled exemplary device with collector 120 in a secured position 123.
FIG. 2b illustrates an assembled exemplary device with collector 120 in a sampling position 124.

FIGS. 2a and 2b illustrate exemplary embodiments of the present invention when assembled. FIG. 2a illustrates a secured position 123 of collector 120, in which the collector can be disposed within sheath 110. FIG. 2b illustrates a sampling position 124 of collector 120, in which the collector can extend outside of, and from, sheath 110. Further, collector 120 can be transitioned between secured and sampling positions via handle 130, with such transitioning being further described herein.

In general operation of the present invention, a biological sampling device 100 can be inserted into an orifice of a target organism (not shown), and collector 120 can be transitioned from a secured position to a sampling position. Collector 120 can be moved via handle 130 so as to abrasively contact an internal portion of the organism and collect biological material therefrom and/or adjacent thereto. Collector 120 can then be transitioned back to a secured position, such that the collector, along with collected biological material, can then be removed from the orifice.

As illustrated in FIG. 1, sheath 110 can be cylindrically shaped. However, sheath 110 can be provided in any desired shape that is functionally compatible with the present invention. Further, sheath 110 can be provided as a combination of multiple shapes, and moreover, need not be uniformly or symmetrically shaped. For example and not in limitation, sheath 110 can be provided in any combination of the following shapes, in whole or in part: cuboid, cylinder, pyramid, cube, sphere, cone, prism, cuboid, and/or any variations thereof, including symmetrical and/or asymmetrical variations thereof. Further, first sheath end 111 can optionally be provided with a rounded and/or a tapered terminal portion to facilitate an insertion of sheath 110 into an orifice of an organism. Also optionally, first sheath end 111 can be petalled so as to have at least one petal 144 (as illustratively shown in FIG. 4 with respect to first applicator end 141), which can assist in an insertion of sheath 110 into an orifice while allowing collector 120 to transition therethrough. Moreover, sheath 110 (and optionally applicator 140, see infra) can be provided in any desired material or materials that provide an overall rigidity that allows, insertion of the sheath into an orifice of an organism, and to the extent desired, deformation of a collector, as further described herein. For example and not in limitation, sheath 110 can be provided in any one or more of the following materials: plastic, metal, ceramic, wood, paper, cardboard, any known or apparent variations thereof, or any other material that is functionally compatible with the present invention. Further, in another exemplary aspect, sheath 110 can be provided with a smooth exterior surface to minimize friction between the exterior surface and internal portions of the organism.

In another exemplary aspect of the present invention, abrasive outer surface area 121 of collector 120 can be sufficiently abrasive such that its movement (e.g., linear motion, vibration, rotation, etc.) against an internal portion of an organism causes the outer surface area 121 to physically contact biological material from, on, or adjacent to the internal portion, and to collect the biological material via a static force, absorption, adhesion, and/or any other desired, foreseeable, or apparent means. Notably, biological matter can be near the internal portion and nonetheless collected. Further, according to the present invention, biological material can include one or more of a cell, a virus, a bacterium, a microorganism, DNA, RNA, or any other type of biological material including a remnant, portion, or byproduct of any of the aforementioned.

According to the present invention, collector 120 can be provided with a symmetric or asymmetric shape when in either a secured or sampling position. As illustrated in FIG. 2a, when in secured position 123, collector 120 can be deformed to have a height, width, and/or diameter that is smaller than that of sheath 110 (or an applicator, as described infra). And as illustrated in FIG. 2b, when in a sampling position 124, outer surface 121 can extend beyond the height, width, and/or diameter of sheath 110. Notably, collector 120 can be formed from any suitable material or materials, which will be apparent to one of ordinary skill in the art given this disclosure. For example, any known or apparent material utilized in obtaining biological samples from within organisms, including but not limited to those suitable for obtaining biological samples for Pap Tests.

In another exemplary aspect of the present invention, changes in the position of outer surface 121 between states can be effectuated by any functionally compatible selection of one or more materials and/or structures of which collector 120 and/or handle 130 is formed. Accordingly, collector 120 can be biased in any mechanic and/or material manner functionally consistent with the present invention.

Figure 3:
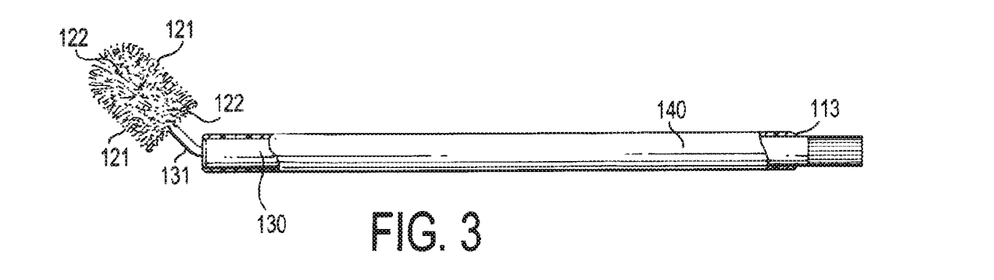
FIG. 3 illustrates an exemplary device having an angled first handle end 131 and a collector 120 having at least one bristle 122.

For example and not in limitation, collector 120 can include a plurality of bristles, a broom, a segment of material, and/or a spatula; and/or can be formed of an elastic material, such as a sponge or a foam material, with the outer portions thereof being outer surface area 121. As illustrated in FIG. 3, collector 120 can include a plurality of bristles 122, the terminal portions of which can form outer surface area 121.

In another exemplary aspect, as illustrated in FIG. 3, collector 120 can include a plurality of bristles 122 that can be materially biased to extend in a linear direction, and mechanically biased to extend outwardly from handle 130 via fixation to first handle end 131. In a further exemplary aspect, bristles 122 can be fixed directly to first handle end 131, or fixed thereto via a ferrule or other type of functionally compatible bristle holder. In another exemplary aspect, when in, or transitioned into, a secured position, collector 120 can deform in shape and/or size to fit within sheath cavity 113 (and/or within an applicator cavity, as described infra). Conjunctively or alternatively, as illustrated in FIG. 3, bias of collector 120 can be achieved via a handle end that is materially and/or mechanically biased towards a non-linear angle, and materially and/or mechanically deformable towards a linear angle that is coaxial with a sheath, such that a collector can be in or transitioned to a secured state within a sheath cavity (and/or within an applicator cavity, as described infra). For example, and not in limitation, first handle end 131 can be formed of an elastic material, such as a metal or plastic, for example and not in limitation, and/or can include a spring or elastic material to effectuate such bias and deformability, for example and not in limitation. Alternatively or conjunctively, collector 120 need not be biased, but rather can be angled with a linear handle 130 so as to reach beyond a height, width, and/or circumference of sheath 110 by angling the handle so as not to be co-axial with the sheath (or applicator, as described infra).

In another exemplary aspect, handle 130 can extend through sheath cavity 113, with first handle end 131 being fixed to collector 120 and second handle end 132 extending from second sheath end 112. In an exemplary aspect, handle 130 can be provided in a linear shape, such as a rod, for example and not in limitation; however, handle 130 can alternatively be provided in any other shape, whether symmetric or asymmetric, as long as the resulting handle is functionally compatible with the present invention. In an additional exemplary aspect, handle 130 can be formed of any suitable material or materials that provide sufficient overall rigidity and strength to allow pushing, pulling, and positional maintenance of collector 130 between or in a secured and/or sampling state, and to allow rotation or movement of a collector when in a sampling state. Notably, in any embodiment of the present invention, pushing and/or pulling of handle 130 can include rotating the handle, such as where the handle is configured to rotate through a threaded guide, such as threads for example and not in limitation, which can provide liner motion through rotation of the handle. In yet a further exemplary aspect, handle 130 can include a motor adapter (not shown) configured to connect to a motor (not shown), such that motorized energy (e.g., one or more of rotation, vibration, pushing, and pulling) can be transferred from the motor to collector 120 via handle 130.

Notably, handle 130 can optionally be configured to disengage from collector 120 (such as, for example and not in limitation, rotational disengagement from a threaded receiver) or can be cut, broken, or otherwise shortened.

Figure 4:
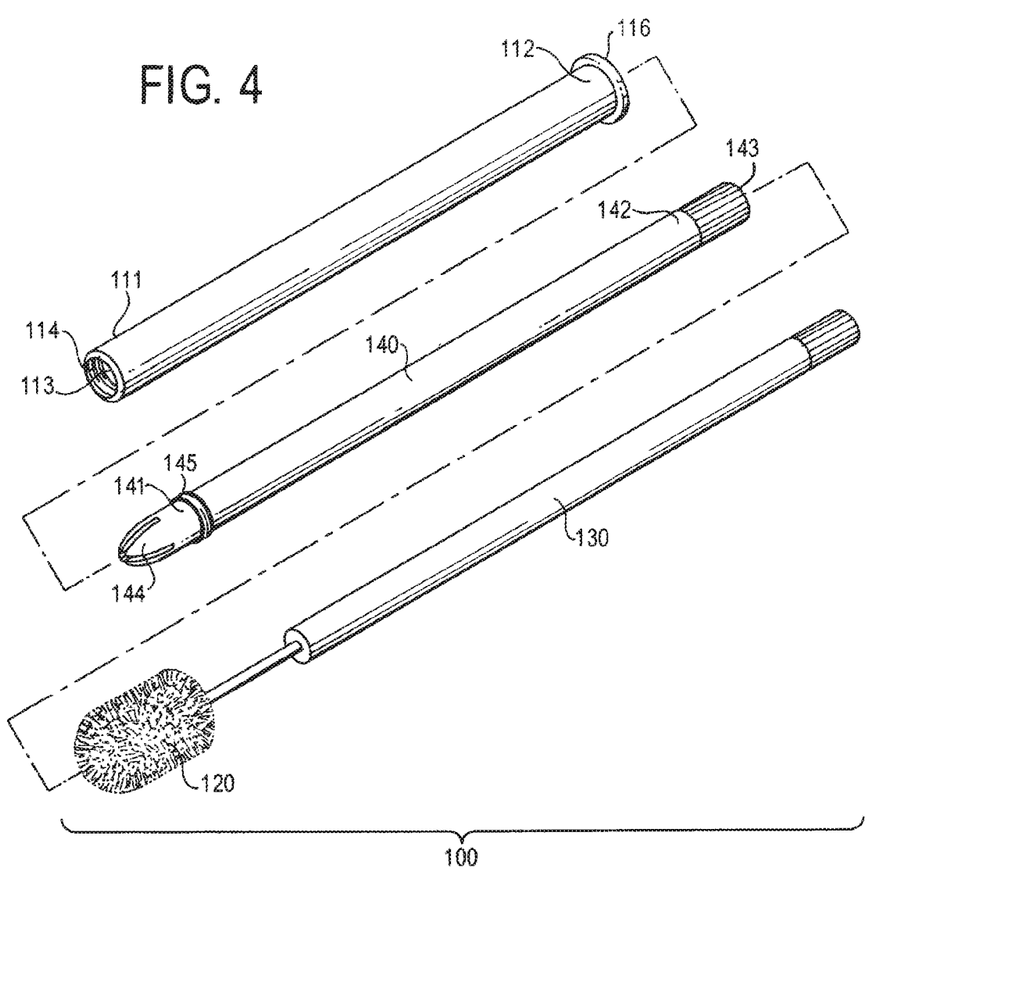
FIG. 4 illustrates an exploded view of another exemplary embodiment of the present invention, in which a biological sampling device 100 can include a sheath 110, a collector 120, a handle 130, and an applicator 140.

FIG. 4 illustrates an exploded view of another exemplary embodiment of the present invention, in which a biological sampling device 100 can further include, in addition to a sheath 110, a collector 120, and a handle 130, and an applicator 140. In an exemplary aspect of the present invention, applicator 140 can have a first applicator end 141, a second applicator end 142, and an applicator cavity 143 that can extend between the first and second applicator ends. As illustrated, applicator 140 can be configured to extend through sheath cavity 113, and handle 130 can be configured to extend through applicator cavity 143. In an exemplary aspect of the present invention, sheath 110 and applicator 140 can be complementarily configured such that the applicator can slidably fit within sheath cavity 113, with collector 120 and handle 130 cooperatively operating as described herein, but additionally, respectively within and through applicator cavity 143.

As illustrated in FIG. 4, applicator 140 can be cylindrically shaped. However, applicator 140 can be provided in any desired shape that is functionally compatible with the present invention. Further, applicator 140 can be provided as a combination of multiple shapes, and moreover, need not be uniformly or symmetrically shaped. For example and not in limitation, applicator 140 can be provided in any combination of the following shapes, in whole or in part: cuboid, cylinder, pyramid, cube, sphere, cone, prism, cuboid, and/or any variations thereof, including symmetrical and/or asymmetrical variations thereof. Further, first applicator end 141 can optionally be provided with a rounded and/or a tapered terminal portion to facilitate an insertion of applicator 140 into an orifice of an organism. Also optionally, first applicator end 141 can be petalled so as to have at least one petal 144. Moreover, applicator 140 can be provided in any desired material or materials that provide an overall rigidity that allows, insertion of the applicator into an orifice of an organism, and to the extent desired, deformation of collector 120. For example and not in limitation, applicator 140 can be provided in any one or more of the following materials: plastic, metal, ceramic, wood, paper, cardboard, any known or apparent variations thereof, or any other material that is functionally compatible with the present invention.

In an exemplary aspect of the present invention, the transitioning (and returning) of collector 120 between states can be effectuated by pushing or pulling handle 130 with sheath 110 and/or applicator 140 being in either a static position or a counter motion relative to the pushing or pulling; and/or by retracting or further inserting sheath 110 and/or applicator 140 with collector 120 being in either a static position or a counter motion relative to the retracting or further inserting. Further, motion of collector 120 while in the sampling position can be effectuated by one or more of the following: linear motion of the collector; motion of the collector to and from the sampling position; vibratory motion of the collector; and rotational movement of the collector.

FIGS. 5*a*-5*d* illustrate additional exemplary embodiments of the present invention when assembled.

Figure 5A:
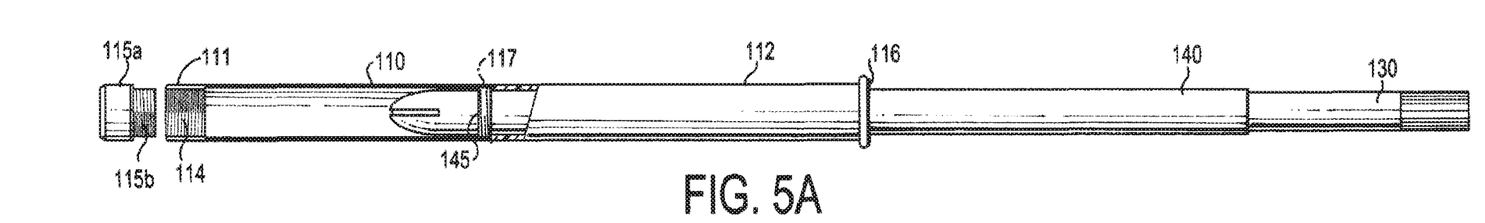
FIG. 5a illustrates a general view of an exemplary device in an exemplary configuration.

FIG. 5*a* illustrates a preliminary configuration of sampling device 100, in which handle 130 can be positioned within applicator cavity 143, and applicator 140 can be positioned within sheath cavity 113. Notably, as further discussed infra, FIG. 5*a* additionally illustrates optional inner sheath threads 114 and cap 115*a* having cap threads 115*b*, which when cooperatively engaged can provide a seal before and/or after a biological sample is obtained.

Figure 5B:
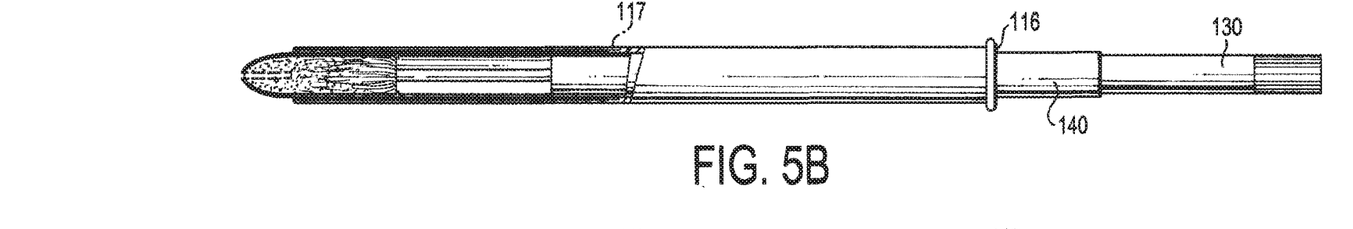
FIG. 5b illustrates an exemplary device in an exemplary pre-use configuration in which collector 120 is in a secured position.

FIG. 5*b* illustrates another preliminary configuration of sampling device 100. As illustrated, prior to deployment, collector 120 can be in a secured position 123, in the collector can be positioned within at least one of sheath 110 and applicator 140. As further illustrated, optionally, first applicator end 141 can extend from first sheath end 111.

Figure 5C:
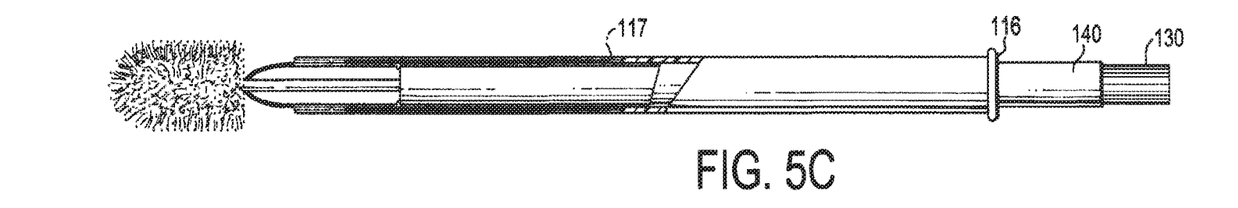
FIG. 5c illustrates an exemplary device in an in-use configuration in which collector 120 is in a sampling position.

FIG. 5*c* illustrates another exemplary embodiment of sample device 100, in which collector 120 has been transitioned from a secured position 123 to a sampling position 124, in which the collector is positioned outside of sheath 110 and applicator 140.

Figure 5D:
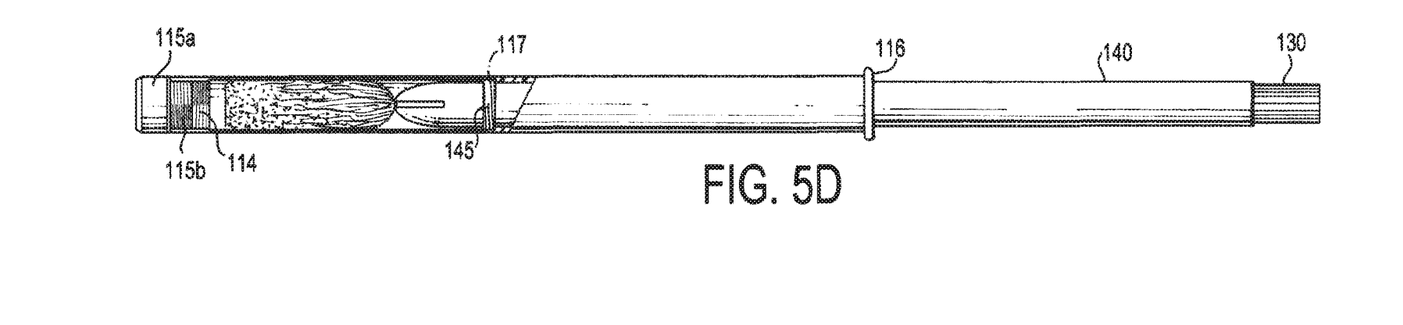

FIG. 5*d* illustrates another exemplary embodiment of sample device 100, in which collector 120 has been transitioned from a sampling position 123 to a secured position 124, with cap 115*a* engaged with sheath 110 via engagement between sheath threads 114 and cap threads 115*b*. Notably, secured position 123 is illustratively shown as collector 120 being positioned within sheath 110 and outside applicator 140. However, it is expressly contemplated that secured position 123 can include collector 120 being within at least one of sheath 110 and applicator 140.

FIGS. 5*a*-5*d* further illustrate optional sheath handle 116, which can assist in the movement and/or positional maintenance of sheath 110 in using sampling device 100; as well as second handle end 132 having a textured outer surface to facilitate manual manipulation thereof.

In additional exemplary embodiments of the present invention, a biological sampling device can optionally include one or more sealing and/or stopping structures at any end of any element of the present invention and/or between any two elements of the present invention. In exemplary aspects of the present invention, a sealing structure can provide a gas and/or liquid-tight seal for retaining and/or excluding a gas and/or liquid; whilst a stopping structure can limit and/or define relative movement between one or more elements of the present invention.

According to the present invention, an exemplary sealing structure can include one or more of an open or closed thread, a cap, a groove, a collar, a gasket, a shoulder, a protrusion, or any other functionally compatible structure or structures that can provide a sealing function. Further, a sealing structure can be provided at one or more of a first sheath end 111, a second sheath end 112, a first applicator end 141, a second applicator end 142, and a first handle end 131, and a second handle end 132, and/or between any two of a sheath 110, a collector 120, a handle 130, and an applicator 140; and thus, can assist in preserving collected biological matter, which can prevent contaminants from entering between seals and/or hold a preserving liquid between seals, for example and not in limitation.

Figure 6A:
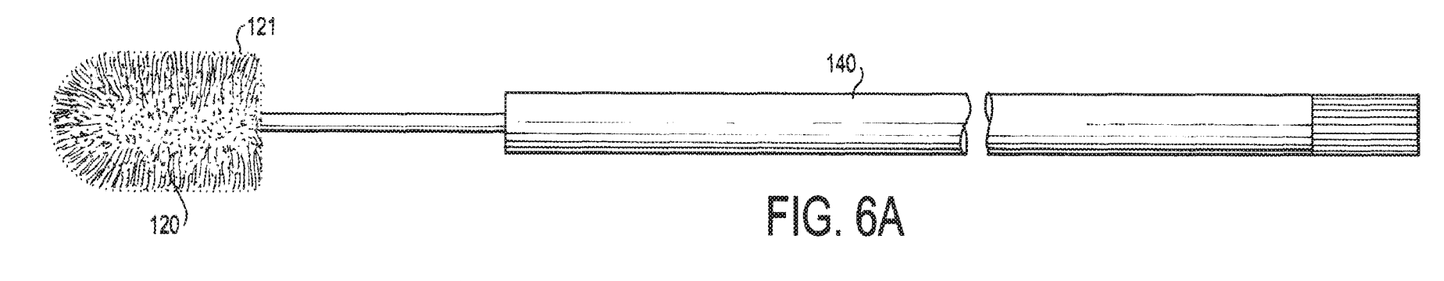
FIG. 6a illustrates an exemplary device with a handle 130 configured to shorten in length.
Figure 6B:
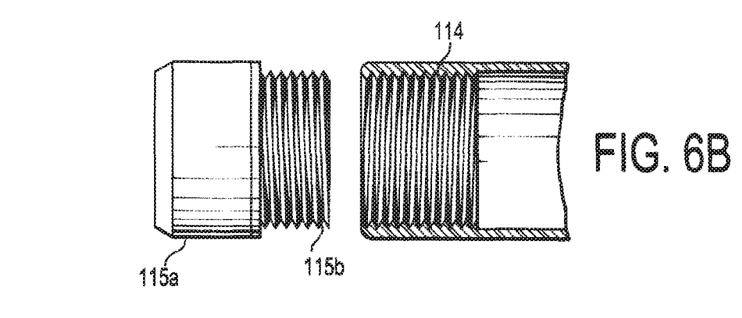
FIG. 6b illustrates a detailed view of an optional and exemplary sealing structure as cap 115a, cap threads 115b, and inner sheath threads 114.

FIGS. 5*a* and 5*d* illustrate an optional sealing structure as sheath end threads 114 at first sheath end 111 and cap 115*a* having cap threads 115*b*, which are additionally illustrated in detailed perspective of FIG. 6*b*. When such threads are engaged together, a desired seal at the first sheath end can be achieved. It should be noted that the present invention contemplates one or more threads being positioned on the inside or outside of any element. Also notably, any end can optionally include an annular groove or collar located on the outside or inside of the end, and a cap can be complementarily configured with a respective collar or groove to sealably engage such groove or collar. Further, a cap and/or an end can include one or more gaskets, such as o-rings, to facilitate a seal.

In another exemplary aspect of the invention, one or more sealing structures can be provided between any two elements of the present invention. FIGS. 5*a* and 5*d* further illustrate another optional sealing structure as inner sheath threads 117 and applicator threads 145, which are additionally illustrated in detailed perspectives of FIGS. 6*c* and 6*d*. When such threads are engaged together, a desired seal between sheath 110 and applicator 140 can be achieved. Notably, when such a seal is effectuated in conjunction with a second seal, such as, for example and not in limitation, via first sheath end 111 and a cap 115*a*, a sealed compartment enclosing collector 120 can be formed. Also notably, such a sealed compartment can be formed between sheath 110 and handle 130, where handle 130 includes handle threads (not shown).

In another exemplary aspect of the present invention, one or more complementary threads can be open, in which case two elements can relatively rotate through each other, or closed, in which case two elements cannot relatively rotate through each other.

In a further exemplary aspect, the inside of a sheath and the outside of an applicator can include a first groove or collar, and the other of the inside of a sheath and the outside of an applicator can include a complementarily configured collar or groove to sealably engage the other groove or collar. Notably, plural collars can be provided in conjunction with threads to enhance a seal. Also optionally, the inside of a sheath and/or the outside of an applicator can include one or more gaskets, such as o-rings, to facilitate a seal.

In another exemplary aspect, the present invention can optionally include one or more stopping structures. Notably, a sealing structure can be strategically positioned to provide such a stopping function, such that movement of elements of the present invention can be limited or prevented in at least one direction before or after sampling. Accordingly, relative movement of two or more elements of the present invention can be strategically defined before and/or during sampling; such as, for example and not in limitation, defining a maximum and/or minimum distance a collector 120 can extend out from sheath 110 and/or applicator 140, defining the maximum and/or minimum distance a collector can move within a sheath and/or collector; limiting how many times a collector can rotate when in a sample position; and/or defining any other limit or range of relative motion of two or more elements of the present invention. Thus, a sealing structure can be provided between any two elements of the present invention for sealing and/or stopping functionality. Moreover, a sealing structure can be provided at any point between, and including, ends of any two elements of the present invention. Further, the present invention is not to be construed as requiring any of the specific sealing and/or stopping structures described herein, and is to be construed as including any known or apparent structure or structures that are functionally compatible with the present invention.

Figure 6C:
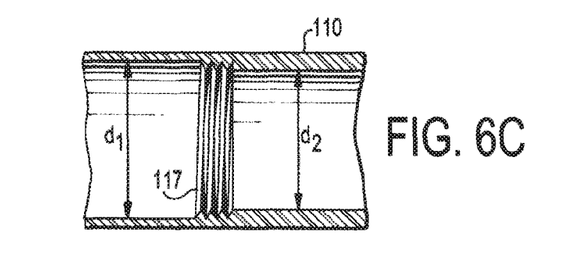
FIG. 6c illustrates a detailed view of an exemplary sheath cavity 113 with a optional and exemplary sealing/stopping structure as inner sheath threads 117, and an optional stopping structure as differing diameter sizes $d_1$, $d_2$ of sheath cavity 113.
Figure 6D:
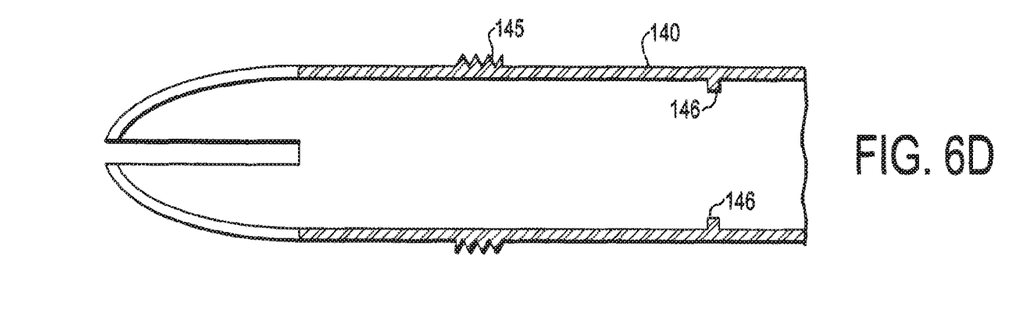
FIG. 6d illustrates an exemplary applicator 140 with an optional and exemplary sealing/stopping structure as applicator threads 145 and another optional and exemplary sealing/stopping structure applicator abutments 146.

For example and not in limitation, FIG. 4 illustrates an optional stopping structure as sheath end threads 114 and applicator threads 145, which can limit relative movement between sheath 110 and applicator 140 when such threads abut each other and when engaged. FIGS. 6c and 6d illustrate a first optional stopping structure as inner sheath threads 117 and applicator threads 145, which can limit relative movement between sheath 110 and applicator 140 as above; and a second optional stopping structure as a decreased diameter of sheath 110 from d1 to d2, such that sheath 110 at d2 can form an abutment for applicator 140 or handle 130 having an diameter dh, where d1>dh>d2. Further, FIG. 6d illustrates at least one applicator inner abutment 146, which can limit relative movement of a complementarily sized handle 130.

Also notably, a sealing structure can be permanent between elements of the present invention that need not move, such as between a handle and a collector. Thus, for example, a sealing structure in this regard can include complementarily configured threads; a molded, glued, or clamped bond therebetween; and/or any other permanent sealing and/or fixation structure or structures.

In another exemplary aspect, sealing and/or stopping functionally between elements of the present invention can be alternatively or conjunctively be effectuated via the shapes of elements or portions thereof. For example and not in limitation, a sheath cavity 113 can be provided with a shape that includes a smaller sized diameter (or size) and a larger sized diameter (or size); and an applicator 140 or a handle 130 (or portion thereof) can be provided with a shape having a first diameter (or size) that is less than the sheath cavity's smaller size and a second diameter (or size) that is greater than the sheath cavity's smaller size. Accordingly, when disposed within sheath cavity 113, applicator 140 or handle 130 can move relative thereto until its larger size meets the sheath cavity's smaller size, with such meeting defining a stopping structure. Further, such meeting portions can be complementarily tapered, for example and not in limitation, to further provide a sealing structure. Accordingly, any two or more adjacent elements of the present invention can be provided with complementary shapes to provide a stopping and/or a sealing structure when particularly positioned. Notably, the present invention contemplates that a stopping structure can include an annular collar, a shoulder, a ridge, and/or a protrusion configured to limit movement of elements in one or more directions, as long as the same does not render the present invention functionally unusable in all manners described herein. In a further exemplary aspect, one or more gaskets can be provided between stopping structures to facilitate a sealing function.

In yet another exemplary aspect of the present invention, sheath 110, handle 130, and/or applicator 140 can be provided with an extension element at respective second ends thereof, so as to facilitate manual manipulation of one or more thereof. For example, as illustrated in FIG. 4, sheath handle 116 can act as an abutment so as to limit the depth in which sheath 110 can be inserted into an organism. Further, an extension element can limit the relative motion between two or more elements of the invention, and/or provide an element handle or grip to facilitate manual manipulation of the invention, which can include any combination of pulling, pushing, rotating, moving, holding in a static position, inserting, and/or removing. In a further exemplary aspect, one or more of a sheath extension, an applicator extension, and/or a handle extension can be configured to abut and/or to lock together with another of a sheath extension, an applicator extension, and a handle extension to limit relative motion thereof in at least one direction. For example and not in limitation, such an abutment and/or locking function can provide a stopping and/or sealing function.

The present invention can also be embodied in methods of using, and of preparing a biological sample from, any biological sampling device enabled herein. Further, the present invention can be embodied in a method of testing a biological sample prepared any biological sampling device enabled herein.

Figure 7:
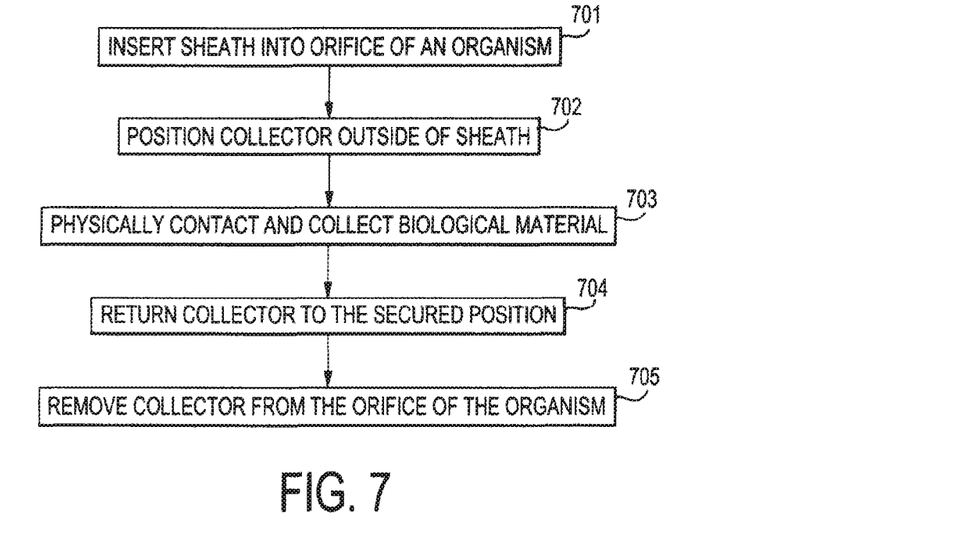
FIG. 7 illustrates exemplary method steps of using a biological testing device having a sheath, a collector, and a handle.

FIG. 7 illustrates an exemplary method of using a biological sampling device having a sheath, a collector, and a handle fixed to the collector to collect a biological sample. According to the present invention, such a method can include the following steps:

inserting the sheath into an orifice of an organism (block 701);

transitioning the collector from a secured position to a sampling position, such that the collector is positioned outside of the sheath (block 702);

via the handle, moving the collector while in the sampling position, such that an outer surface of the collector abrasively moves against an internal portion of the organism to physically contact and collect biological material (block 703); returning the collector from the sampling position to the secured position (block 704); and removing the collector from the orifice of the organism (block 705).

In an exemplary aspect of the invention, optionally, during the insertion step (block 701) and/or the withdrawing step (block 705), the collector can be maintained in a secured position (i.e., within the sheath cavity) to reduce the risk of contaminants being collected by the collector.

In additional exemplary aspects, the collector can be inserted into the sheath after the sheath is inserted into an orifice, and/or the collector can be withdrawn from the sheath (and an orifice) while the sheath is still inserted in the orifice. Such an insertion and/or withdrawal can also reduce the risk of contaminants being collected by collector.

Figure 8:
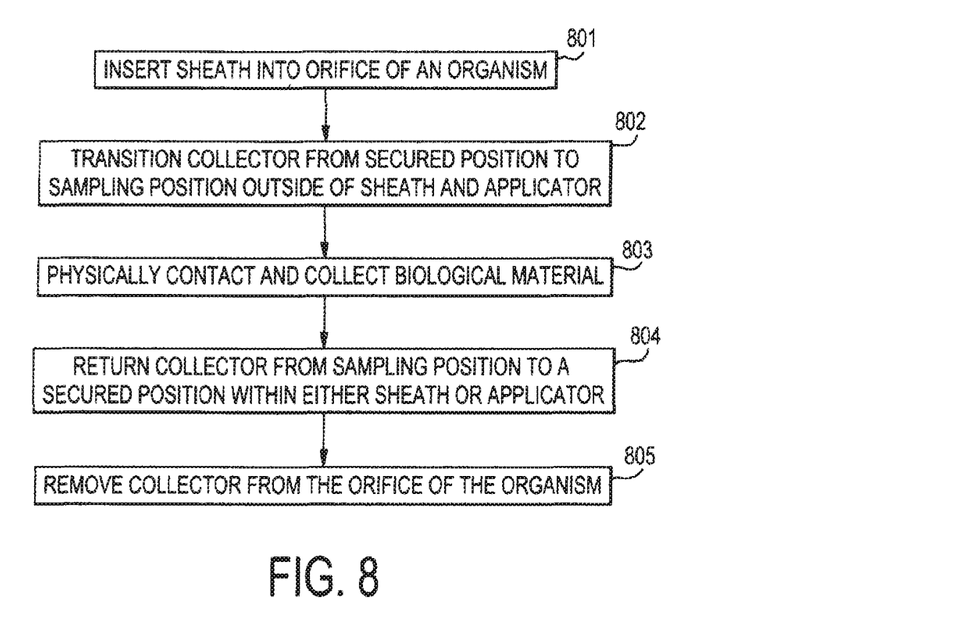
FIG. 8 illustrates exemplary method steps of using a biological testing device having a sheath, an applicator, a collector, and a handle.

FIG. 8 illustrates an exemplary method of using a biological sampling device having a sheath, a collector, a handle fixed to the collector, and an applicator to collect a biological sample. According to the present invention, such a method can include the following steps:

inserting the first applicator end (as illustrated in FIG. 5b) into an orifice of an organism (block 801);

transitioning the collector from a pre-sampling configuration to a sampling configuration (as illustrated in FIG. 5c), such that the collector is positioned outside of the sheath (block 802);

via the handle, moving the collector while in the sampling configuration, such that an outer surface of the collector moves against the biological material to collect the biological material (block 803);

transitioning the device from the sampling configuration to a post-sampling configuration (as illustrated in FIG. 5d) in which the collector and first applicator end are moved through the first sheath end and into the sheath cavity with the sheath being in a static position (block 804); and with the device in the post-sampling configuration, withdrawing the device from within the organism (block 805).

In an exemplary aspect of the invention, optionally, during the insertion step (block 801) and/or the removal step (block 805), the collector can be maintained in the secured position to reduce the risk of contaminants being collected by the collector.

In additional exemplary aspects, the collector can be inserted into the sheath and/or the applicator after the sheath is inserted into an orifice, and/or the collector can be withdrawn from the sheath and/or the applicator while the sheath and/or applicator is still inserted in the orifice. Such an insertion and/or withdrawal can also reduce the risk of contaminants being collected by collector.

Notably, for clarity, with any embodiment of a device 100 enabled herein, a collector can be positioned inside a sheath and/or an applicator when or after the sheath and/or applicator is inserted into an orifice of an organism; a collector can be adapted to remain within a sheath and/or an applicator when the collector is withdrawn from an orifice of an organism; and a collector can be configured to be withdrawn from an orifice of an organism while a sheath and/or an applicator remains inserted in an orifice of an organism.

Figure 9:
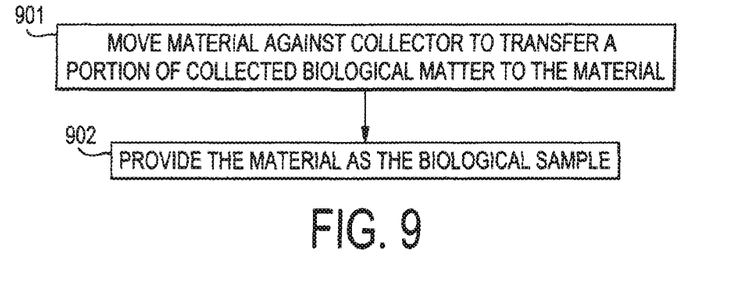
FIG. 9 illustrates exemplary method steps of preparing a biological sample from biological material collected by a biological sampling device having a sheath, a collector with the collected biological material, and a handle fixed to the collector.

FIG. 9 illustrates an exemplary method of preparing a biological sample from biological material collected by a biological sampling device having a sheath, a collector with the collected biological material, and a handle fixed to the collector. According to the present invention, such a method can include the following steps:

moving a transfer material against the collector to transfer at least a portion of the collected biological material to the transfer material (block 901); and after the step of moving, providing the transfer material and the at least a portion of the collected biological material as the biological sample (block 902).

Figure 10:
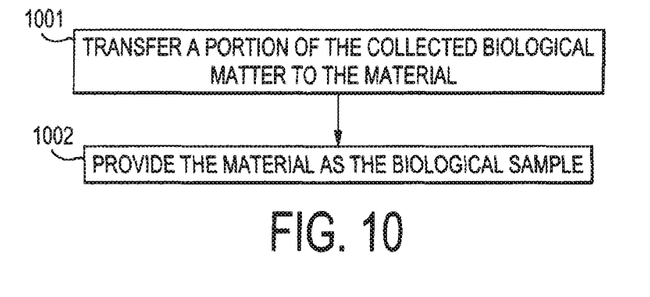
FIG. 10 illustrates exemplary method steps of preparing a biological sample from biological material collected by a biological sampling device having a sheath, an applicator, a collector with the collected biological material, and a handle fixed to the collector.

FIG. 10 illustrates an exemplary method of preparing a biological sample from biological material collected by a biological sampling device having a sheath, an applicator, a collector with the collected biological material, and a handle fixed to the collector. According to the present invention, such a method can include the following steps:

moving a transfer material against the collector to transfer at least a portion of the collected biological material to the transfer material (block 1001); and after the step of moving, providing the transfer material and the at least a portion of the collected biological material as the biological sample (block 1002).

In an exemplary aspect of the present invention, with any method of preparing a biological sample, the transfer material can include a liquid, gas, or solid. In another exemplary aspect of the present invention, optionally, any method of preparing a biological sample can further include a step of introducing a liquid to the biological material to provide a visual indication of a logical state, such as the presence or absence of one or more particular biological states or identities, for example and not in limitation.

Figure 11:
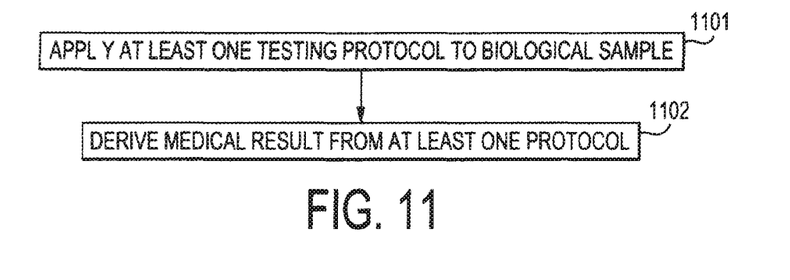
FIG. 11 illustrates exemplary method steps of testing a biological sample obtained from a biological sampling device having a sheath, a collector with collected biological material, and a handle fixed to the collector.

FIG. 11 illustrates an exemplary method of testing a biological sample obtained from a biological sampling device having a sheath, a collector with collected biological material, and a handle fixed to the collector. According to the present invention, such a method can include the following steps:

applying at least one testing protocol to the biological sample (block 1101); and deriving a testing result from the at least one protocol (block 1102).

Figure 12:
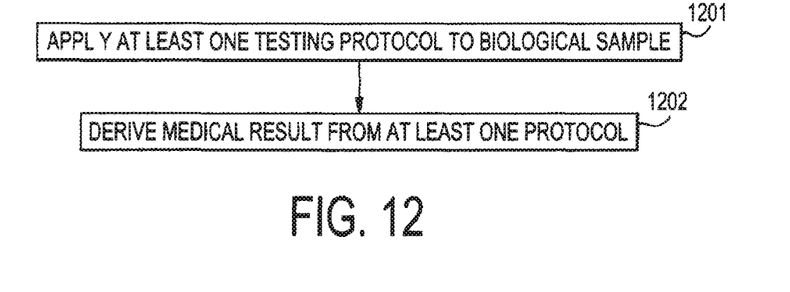
FIG. 12 illustrates exemplary method steps of testing a biological sample obtained from a biological sampling device having a sheath, an applicator, a collector with collected biological material, and a handle fixed to the collector.

FIG. 12 illustrates an exemplary method of testing a biological sample obtained from a biological sampling device having a sheath, an applicator, a collector with collected biological material, and a handle fixed to the collector. According to the present invention, such a method can include the following steps:

applying at least one testing protocol to the biological sample (block 1101); and deriving a testing result from the at least one protocol (block 1102).

In an exemplary aspect of the present invention, a testing protocol can include any known or apparent medical, including future-developed, testing protocol that is functionally consistent with the present invention. For example and not in limitation, such a testing protocol can be associated with a Papanicolaou Test.

Figure 13:
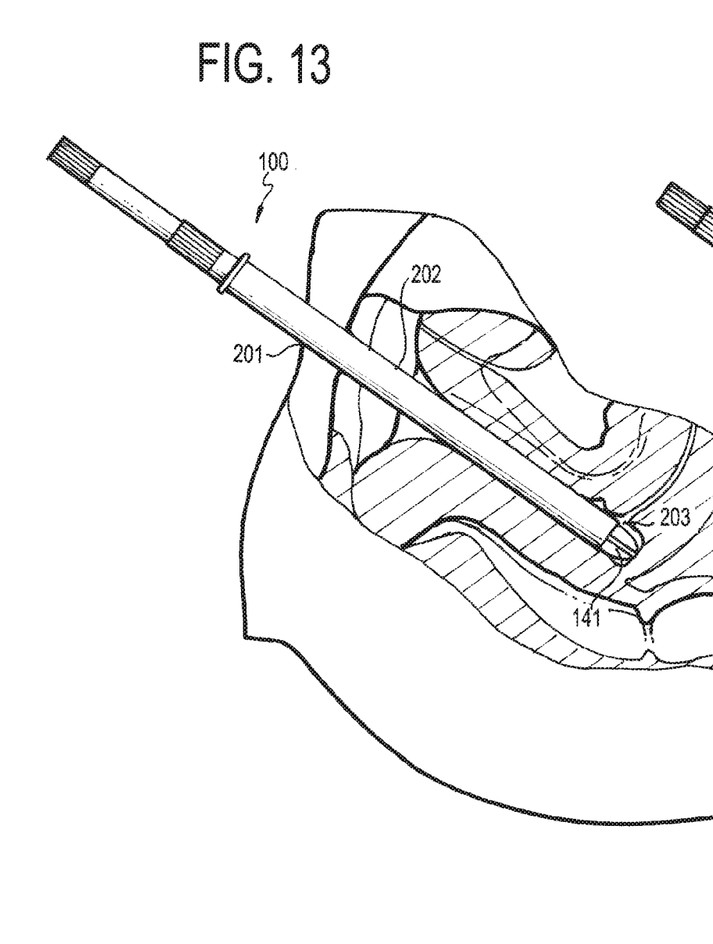
FIG. 13 illustrates an exemplary biological testing device 100 inserted into a vaginal canal 202 of an organism with a collector 120 being in an exemplary secured position.
Figure 14:
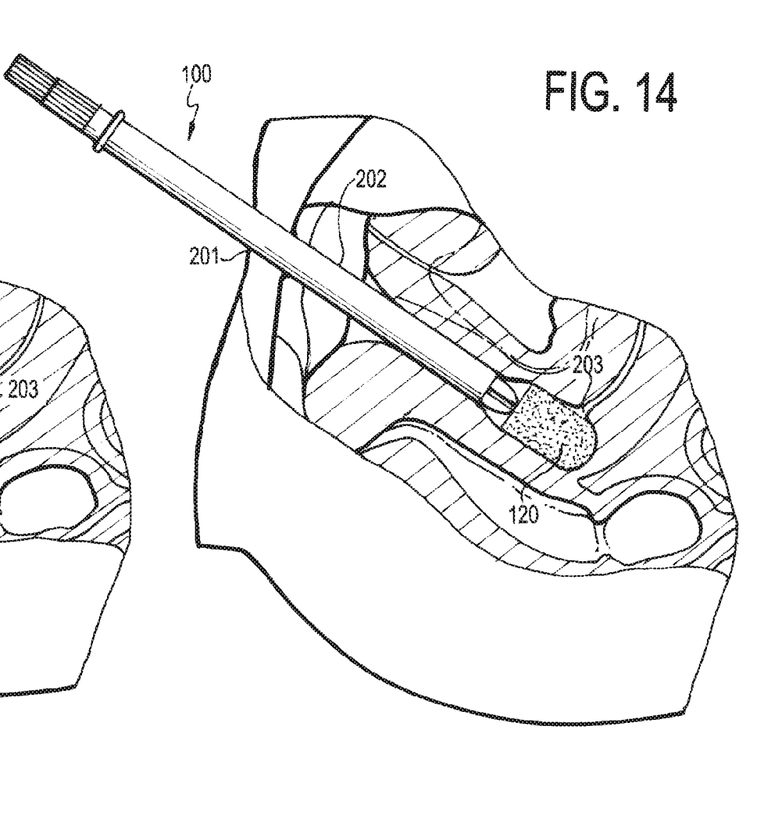
FIG. 14 illustrates an exemplary biological testing device 100 inserted into a vaginal canal 202 of an organism with a collector 120 being in an exemplary sampling position.

It should also be noted that with any embodiment of the present invention, a sampling device 100 can be inserted into an orifice of an organism to varying depths so as to strategically deploy collector 120 at an optimal position within the organism, and therefore, can be provided in varying lengths. For example, and not in limitation, a sampling device 100 can be inserted to a particular depth so as to deploy a collector to collect cells at a known area of concern. For example and not in limitation, as illustrated in FIGS. 13 and 14, a sampling device 100 can be inserted through a human vaginal opening 201 and into a vaginal canal 202 until a first applicator end 141 (and/or a first sheath end 111) abuts the end of the vaginal canal, such that a collector 120 can be optimally deployed where a cervix 203 is located.

Also notably, in any embodiment of the present invention, the overall width, height, and/or circumference of a sampling device 100 can vary in light of the size of a target orifice. In another exemplary aspect, the overall width, height, and/or circumference of a sampling device 100 can be minimized to reduce discomfort to an organism when the device is inserted through an orifice.

It should be noted that this disclosure includes a plurality of elements and/or aspects, and such elements and/or aspects need not necessarily be interpreted as being conjunctively required by one or more embodiments of the present invention. Rather, all combinations of the one or more elements and/or aspects may enable a separate embodiment of the present invention, which may be claimed with particularity in this or any other future filed patent application. Moreover, any particular material, structure, and/or size disclosed herein are to be construed strictly as illustrative and enabling, and not necessarily limiting. Therefore, it is expressly set forth that such materials, structures, and/or sizes independently, or in any combination of one of more thereof, are merely illustratively representative of one or more embodiments of the present invention and are not to be construed as necessary in a strict sense.

Further, to the extent the same aspect, element, or limitation is defined differently anywhere within this disclosure, the broader definition is to attach, with the distinctions encompassed by the narrower definition to be strictly construed as optional.

It will be apparent to one of ordinary skill in the art that the manner of making and using the present invention has been adequately disclosed in the above-written description of the exemplary embodiments, elements, and aspects, independently and in combination with the illustrative drawings attached hereto.

It should be understood, however, that the invention is not necessarily limited to the specific embodiments, aspects, arrangement, and components shown and described above, but may be susceptible to numerous variations within the scope of the invention. Accordingly, the specification and drawings are to be regarded in an illustrative and enabling, rather than a restrictive, sense.

Express Recapture: Insofar as any amendments, characterizations, or other assertions previously made (in the instant application or in any related patent applications or patents, whether a parent, sibling, or child) with respect to any enabled embodiment of the present invention or to any art, whether prior or otherwise, could be construed as any type of disclaimer of any subject matter supported by the disclosure of the instant application, Applicant hereby expressly rescinds and retracts such disclaimer. Applicant also respectfully submits that any prior art previously considered in any related patent applications or patents, including any parent, sibling, or child, may need to be re-visited.

Therefore, it will be understood that the above description of the embodiments of the present invention are susceptible to various modifications, changes, and adaptations, and the same are intended to be comprehended within the meaning and range of equivalents of the respectively described embodiments, elements, aspects, and steps.

Therefore, I claim:

1. A method of obtaining biological material via a biological sampling device, the device comprising a sheath having a first sheath end, a second sheath end, and a sheath cavity that extends between the first and second sheath ends, an applicator having first and second applicator ends, and an applicator cavity that extends between the first and second applicator ends, the applicator being disposed within the sheath cavity, a collector having an abrasive outer surface area, and a handle, having a first handle end and a second handle end, and extending through the sheath and applicator cavities with the first handle end being fixed to the collector and the second handle end extending from the second sheath and second applicator ends, said method comprising steps of:
   a. when the device is in a pre-sampling configuration such that the first applicator end extends beyond the first sheath end and the collector is disposed within the applicator cavity, inserting the device into an organism via an orifice of the organism;
   b. with the device disposed within the organism, transitioning the device from the pre-sampling configuration to a sampling configuration by moving the applicator towards the second handle end with the collector being in a static position such that the collector extends through and beyond the first applicator end and is positioned outside of the applicator and sheath cavities;
   c. with the device in the sampling configuration, via the handle, moving the collector against the biological material within the organism to collect the biological material;
   d. with the device within the organism, transitioning the device from the sampling configuration to a post-sampling configuration by moving the collector and the first applicator end through the first sheath end and into the sheath cavity; and
   e. with the device in the post-sampling configuration, withdrawing the device from within the organism.

2. A method of preparing a biological sample from the biological material collected via the method of obtaining of claim 1, said method of preparing comprising steps of:
   moving a transfer material against the collector to transfer at least a portion of the collected biological material to the transfer material; and
   after said step of moving, providing the transfer material and the at least a portion of the collected biological matter as the biological sample.

3. The method of claim 2, wherein the transfer material includes at least one of a liquid and a solid.

4. A method of testing a biological sample prepared via the method of preparing of claim 2, said method of testing comprising:
   applying at least one testing protocol to the biological sample; and
   deriving a testing result from the at least one protocol.

5. The method of claim 4, wherein the testing protocol relates to a Papanicolaou Test.

* * * * *